United States Patent [19]

Weisburg et al.

[11] Patent Number: 5,403,710
[45] Date of Patent: Apr. 4, 1995

[54] NUCLEIC ACID PROBES AND METHODS FOR DETECTING PATHOGENIC CANDIDA YEASTS

[75] Inventors: William G. Weisburg, Milford; Susan M. Barns, Hopkinton; David J. Lane, Milford; Jeffrey F. Lemontt, West Newton, all of Mass.

[73] Assignee: Amoco Corporation, Naperville, Ill.

[21] Appl. No.: 76,283

[22] Filed: Jun. 11, 1993

Related U.S. Application Data

[63] Continuation of Ser. No. 420,579, Oct. 12, 1989, abandoned.

[51] Int. Cl.⁶ .................. C12Q 1/68; C12P 19/34; C12N 1/00; C07H 17/00
[52] U.S. Cl. ..................... 435/6; 935/91.1; 935/270; 935/921; 935/922; 935/923; 935/924; 536/24.32; 536/24.33; 536/25.3; 435/77; 435/78
[58] Field of Search .............. 435/6, 921, 922, 923, 435/924, 91.1, 270, 91; 536/24.32, 24.33, 25.3; 935/77, 78

[56] References Cited

U.S. PATENT DOCUMENTS 4,358,535  11/1982  Falkow et al. .................. 435/5
4,683,195  7/1987  Mullis et al. .................. 435/6

FOREIGN PATENT DOCUMENTS 0272009  11/1987  European Pat. Off. .
0272009  6/1988  European Pat. Off. .

OTHER PUBLICATIONS

RN 106441-23-0.
RN 102189-03-7.
RN 143911-04-0.
RN 129837-60-1.
RN 145711-68-8.
RN 142157-31-1.
Genbank X56678 (9CI).
RN 140804-48-4.
Kohne, D. E. "The Use of DNA Probes to Detect and Identify Microorganisms," pp. 11–35, *Rapid Methods in Clinical Microbiology* (Plenum Press 1989).
Nelles, L., et al., *Nuc. Acids Res.*, 12:8749–68 (1984).
Olsen, G. J. et al., *Nuc. Acids Res.*, 11:8037–49 (1983).
Tenover, F. C., Chapter 17 (pp. 119–127), *Manuel of Clinical Microbiology* (5th ed., Balows et al., ed. 1991).
Zweib, C., et al., *Nuc. Acids Res.*, 9:3621–40 (1981).
Yoshida et al., *J. Bacteriol* 1990 172(2), 6942–9; Computergenerated sequence comparison.
Rogan et al. *Mol. Biol. Evol.* 4, 327–342 (1987), computer printout only.
Fox et al., *J. Infect. Dis.*, 159:488–494 (Mar. 1989).
Cheung et al., *Diagh. Microbiol.Infect. Dis.*, 10:171–179 (1988).

*Primary Examiner*—Margaret Parr
*Assistant Examiner*—Bradley Lounsbury Sisson
*Attorney, Agent, or Firm*—Norval B. Galloway

[57] ABSTRACT

Nucleic acid probes are described for detecting yeasts capable of causing Candida infection, specifically yeasts of the genera Candida, Torulopsis, and Yarrowia. The preferred probes are complementary to ribonucleic acid sequences unique to specific Candida species, or groups of such species, and as such can detect the rRNA, rDNA, or polymerase chain reaction amplification products of these genes. Methods for detecting the etiological agent of human Candida fungemia utilizing these probes are also provided.

9 Claims, 1 Drawing Sheet

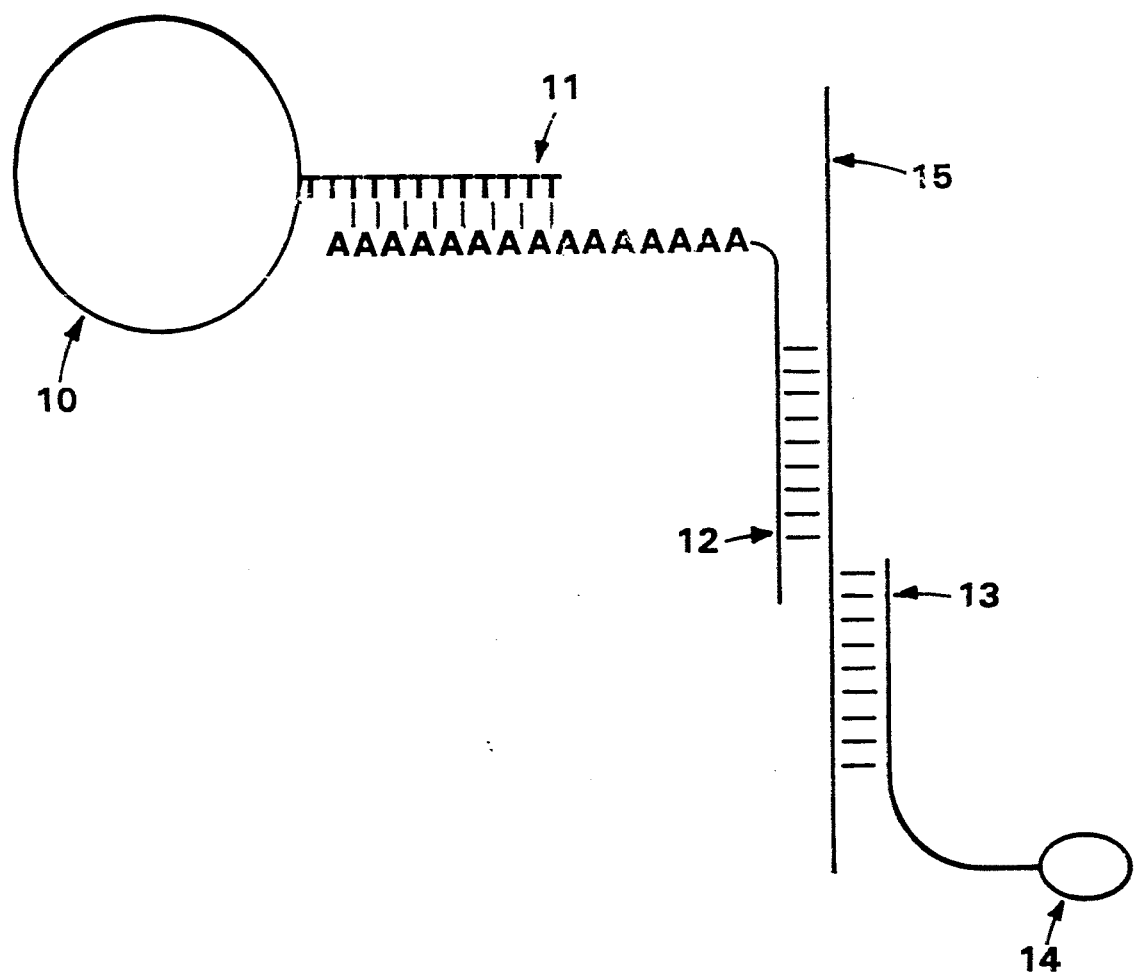

NUCLEIC ACID PROBES AND METHODS FOR DETECTING PATHOGENIC CANDIDA YEASTS

This is a continuation of application Ser. No. 420,579, filed Oct. 12, 1989, now abandoned.

FIELD OF THE INVENTION

This invention relates to the detection of yeasts belonging to the genus Candida. More specifically, it provides nucleic acid probes and compositions along with methods for their use for the specific detection and identification of Candida yeasts.

BACKGROUND OF THE INVENTION

Candida species are yeasts, that is fungi with a predominantly unicellular form of development, according to one source (Odds, F. C., Candida and Candidosis, 2nd Edition, W. B. Saunders, London, 1988). According to this same source, "The genus Candida as a whole comprises more than 150 species, whose main common feature is the absence of any sexual form." It is a "default" genus, and consequently the pathogenic medically significant species represent a small subset of an extremely heterogeneous taxon. As obvious from the list below, the taxonomy of this group still employs several different names to imply the same species.

Ten species of Candida yeasts are commonly recognized as causing a significant fraction of all human fungal infection:

- Candida albicans (including Candida stellatoidea)
- Candida tropicalis (including Candida paratropicalis)
- Torulopsis (Candida) glabrata
- Candida parapsilosis
- Candida lusitantae
- Candida krusei
- Candida guilliermondii
- Candida kefyr (pseudotropicalis)
- Candida viswanathii
- Yarrowia (Candida) lipolytica Candida albicans is by far the most important fungal pathogen both in terms of numerical prevalence and pathogenicity. Following Candida albicans, the next most important pathogenic species are Candida tropicalis, Candida parapsilosis, and Torulopsis glabrata.

Candida infections, also termed "candidosis", "candidiasis", or "Candida mycosis", of virtually every tissue in the human body have been reported. Superficial infections of mucosal surfaces—that is "thrush"—are the most common type. But, it is the systemic and deep tissue infections that are the most serious and life threatening.

Candidas are considered opportunistic pathogens. The organisms are widely distributed in nature. The immune-compromised population, including AIDS/HIV infected individuals and cancer patients, is particularly susceptible to Candida infection. When Candida infection occurs systemically, mortality rates are high. Consequently, early detection of fungal septicemia (fungemia) and prompt administration of antifungal chemotherapy, such as Amphotericin B, is crucial.

All of the currently accepted Candida yeast diagnostic methods rely on culture followed by biochemical characterization to identify particular species. For example, colonies might be grown from a blood sample employing the DuPont Isolator, on a Sabouraud's glucose agar plate. The purified colony could be identified by, for example, Analytab Products' API 20C yeast identification system. This entire procedure typically requires around six days.

It is an aspect of the present invention to provide nucleic acid probes complementary to unique nucleic acid sequences associated with Candida yeast pathogens.

It is another aspect of the present invention to provide rapid diagnostic assays utilizing nucleic acid probes for assessing the presence of Candida yeasts in a clinical sample.

It is still another aspect of the present invention to provide probes which can hybridize to target regions which can be rendered accessible to probes under normal assay conditions.

While Kohne et al. (Biophysical Journal 8:1104–1118, 1968) discuss one method for preparing probes to rRNA sequences, they do not provide the teaching necessary to make Candida yeast probes or any other probes to detect fungi.

Pace and Campbell (Journal of Bacteriology 107:543–547, 1971) discuss the homology of ribosomal ribonucleic acids from diverse bacterial species and a hybridization method for quantitating such homology levels. Similarly, Sogin, Sogin and Woese (Journal of Molecular Evolution 1:173–184, 1972) discuss the theoretical and practical aspects of using primary structural characterization of different ribosomal RNA molecules for evaluating phylogenetic relationships. Fox, Pechman and Woese (International Journal of Systematic Bacteriology 27:44–57, 1977) discuss the comparative cataloging of 16S ribosomal RNAs as an approach to prokaryotic systematics. These references, however, fail to relieve the deficiency of Kohne's teaching with respect to fungi, and in particular, do not provide specific probes useful in assays for detecting Candida fungemia or its etiological agent, members of the genus Candida.

Ribosomes are of profound importance to all organisms because they serve as the only known means of translating genetic information into cellular proteins, the main structural and catalytic elements of life. A clear manifestation of this importance is the observation that all cells have ribosomes.

Bacterial ribosomes contain three distinct RNA molecules which, at least in Escherichia coli, are referred to as 5S, 16S and 23S rRNAs. In eukaryotic organisms, their are four distinct rRNA species, generally referred to as 5S, 18S, 28S, and 5.8S. These names historically are related to the size of the RNA molecules, as determined by their sedimentation rate. In actuality, however, ribosomal RNA molecules vary substantially in size between organisms. Nonetheless, 5S, 18S, 28S, and 5.8S rRNA are commonly used as generic names for the homologous RNA molecules in any eukaryote, and this convention will be continued herein.

As used herein, probe(s) refer to synthetic or biologically produced nucleic acids (DNA or RNA) which, by design or selection, contain specific nucleotide sequences that allow them to hybridize under defined predetermined stringencies, specifically (i.e., preferentially, see next paragraph) to target nucleic acid sequences. In addition to their hybridization properties, probes also may contain certain constituents that pertain to their proper or optimal functioning under particular assay conditions. For example, probes may be modified to improve their resistance to nuclease degradation (e.g. by end capping), to carry detection ligands (e.g. fluorescein, 32-P, biotin, etc.), or to facilitate their capture onto a solid support (e.g., polydeoxyadenosine "tails"). Such modifications are elaborations on the basic probe function which is its ability to usefully discriminate between target and non-target organisms in a hybridization assay.

Hybridization traditionally is understood as the process by which, under predetermined reaction conditions, two partially or completely complementary strands of nucleic acid are allowed to come together in an antiparallel fashion (one oriented 5' to 3', the other 3' to 5') to form a double-stranded nucleic acid with specific and stable hydrogen bonds, following explicit rules pertaining to which nucleic acid bases may pair with one another. The high specificity of probes relies on the low statistical probability of unique sequences occurring at random as dictated by the multiplicative product of their individual probabilities. These concepts are well understood by those skilled in the art.

The stringency of a particular set of hybridization conditions is determined by the base composition of the probe/target duplex, as well as by the level and geometry of mispairing between the two nucleic acids.

Stringency may also be governed by such reaction parameters as the concentration and type of ionic species present in the hybridization solution, the types and concentrations of denaturing agents present, and the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will dictate certain characteristics of the preferred probes to be employed. Such relationships are well understood and can be readily manipulated by those skilled in the art.

As a general matter, dependent upon probe length, such persons understand stringent conditions to mean approximately 35° C.–65° C. in a salt solution of approximately 0.9 molar.

SUMMARY OF THE INVENTION

In accordance with the various principles and aspects of the present invention, there are provided nucleic acid probes and probe sets comprising deoxyribonucleic acid (DNA) or ribonucleic acid (RNA) sequences which hybridize, under specific conditions, to the ribosomal RNA molecules (rRNA) or rRNA genes (rDNA) of pathogenic Candida yeasts but which do not hybridize, under the same conditions, to the rRNA or rDNA of other fungi or bacteria which may be present in test samples. The probes of the present invention now permit the development and implementation of a valuable nucleic acid hybridization assay for the specific detection of Candida fungemia or its etiological agents. This assay may be advantageously used to test clinical samples of blood, urine, cerebrospinal fluid, skin biopsy, saliva, synovial fluid, sputum, bronchial wash, bronchial lavage, or other tissue or fluid samples from human patients or veterinary subjects.

Nucleic acid hybridization based assays have been discovered to impart enhanced performance capabilities with respect to most currently available, microbiological or immunological methods for detection of fungi in test samples, generally including:

a) increased sensitivity; i.e., the ability to detect said yeast in a given sample more frequently;

b) potentially significant reductions in assay cost due to the use of inexpensive reagents and reduced labor;

c) accurate identification of even biochemically unusual strains of the target organism, or isolates with dramatically different antigenic properties;

d) direct assay for the presence of the yeast and consequent potential to quantify the etiological agents;

e) direct testing allows the monitoring of the efficacy of an antifungal regime; and f) potentially significant reductions in the exposure of laboratory technologists to bodily fluid specimens harboring infectious agents.

It has been discovered that other advantages incurred by directing the probes of the present invention against rRNA include the fact that the rRNAs detected constitute a significant component of cellular mass.

Although estimates of cellular ribosome content vary, actively growing Candida yeasts may contain upwards of 100,000 ribosomes per cell, and therefore 100,000 copies of each of the rRNAs (present in a 1:1:1:1 stoichiometry in ribosomes). In contrast, other potential cellular target molecules such as genes or RNA transcripts thereof, are less ideal since they are present in much lower abundance. A further unexpected advantage is that the rRNAs (and the genes specifying them) appear not to be subject to lateral transfer between contemporary organisms. Thus, the rRNA primary structure provides an organism-specific molecular target, rather than a gene-specific target as would likely be the case, for example of a plasmid-borne gene or product thereof which may be subject to lateral transmission between contemporary organisms.

The discovery that probes could be generated with the extraordinary inclusivity and exclusivity characteristics of those of the present invention with respect to the detection of the etiological agents of Candida fungemia was unpredictable and unexpected.

All references made herein are fully incorporated by reference.

BRIEF DESCRIPTION OF THE TABLE AND FIGURE

Further understanding of the principles and aspects of the present invention may be made by reference to the table wherein:

Table 1 displays the hybridization behavior of three probes toward a panel of clinically representative Candida species and other fungi, human, wheat, stool RNA, and two ubiquitous bacterial species. All species on the panel are represented by 100 ng of purified, denatured RNA. Probes were 32-Phosphorous labelled, hybridized to panels under standard conditions, and autoradiographically evaluated. "+" represents strong hybridization signal after three hours exposure, "+ —" is a weak signal, "+ —" is virtually absent, and "—" is indicative of no hybridization of probe to target.

And wherein the FIGURE schematically represents a dual probe capture/detector assay.

DETAILED DESCRIPTION OF THE INVENTION AND BEST MODE

Probe Development Strategy

Determination of the 18S rRNA sequence from the type strain of the following Candida species was done by standard laboratory methods known to those skilled in the art:

*Candida albicans* (ATCC 18804)
*Candida tropicalis* (ATCC 750)
*Torulopsis* (Candida) *glabrata* (ATCC 2001)

*Candida parapsilosis* (ATCC 22019)
*Candida lusitaniae* (ATCC 42720)
*Candida krusei* (ATCC 6258)
*Candida guilliermondii* (ATCC 6260)
*Candida kefyr* (pseudotropicalis) (ATCC 4135)
*Candida viswanathii* (ATCC 22981)
*Yarrowia* (Candida) *lipolytica* (ATCC 18942)

Numbers in parentheses represent the strain number as designated by the American Type Culture Collection, Rockville, Md. Subsequent comparison to sequences of other fungal 18S rRNAs was discovered to narrow considerably the search for worthwhile target sequences within the 18S rRNA. Interesting target sequences were defined as those containing clustered mismatches when compared to known and newly determined non-Candida ribosomal sequences. Probes were designed so as to optimize the distribution of mismatches between probe and non-Candida rRNA. Additional evaluation of 18S rRNA sequences from other significant fungemia-causing organisms also contributed to ultimate probe design.

Physical Description of the Probes

The probe selection strategy yielded sixteen probes useful for assaying and identifying Candida yeasts in samples and include the following preferred oligonucleotide probes:
PROBE 1349: 5'-TCC-TGG-TTC-GCC-ATA-AAT-GGC-TAC-CCA-GAA-3'
PROBE 1350: 5'-AGG-TAA-GGC-CCG-GGT-GCA-TTC-CAG-TAC-ACG-3'
PROBE 1353: 5'-CGA-CAT-AAA-ATC-GGA-CCG-GCC-AAC-CAG-ACC-3'
PROBE 1351: 5'-CAA-TTA-CAA-GAC-CtA-AGG-CCC-TGT-ATC-GTT-3'
PROBE 1355: 5'-GCG-CGC-CAG-ACA-AGG-CTA-GCG-GCG-CTA-TTT-3'
PROBE 1421: 5'-GCC-AAA-CAC-CAC-AAG-GGC-GAA-TGG-TTA-GCC-3'
PROBE 1453: 5'-GTC-ATG-TAT-TAG-TTC-TGA-AGT-TAT-CAC-GGT-3'
PROBE 1346: 5'-TCG-GTT-CCA-GAA-TGA-GGT-TGC-CCC-CTT-TCC-3'
PROBE 1354: 5'-CTC-GGT-TGG-GTC-CAG-TAC-GCA-TCA-GAA-AGA-TGG-3'
PROBE 1358: 5'-CTC-TAA-GAA-GTG-ACT-ATA-CCA-GCA-AAT-GCT-3'
PROBE 1529: 5'-GGC-TCG-GCT-GGG-TCC-AGT-ACG-CAT-CAA-AAA-GAT-GGA-TT-3'
PROBE 1536: 5'-TCA-AAA-AAG-ATG-GAC-CGG-CCA-AGC-CAA-GCC-T-3'
PROBE 1534: 5'-CTG-GTT-CGC-CAA-AAG-GCT-AGC-CAG-AAG-GAA-T-3'
PROBE 1535: 5'-CTG-GTT-CGC-CAA-AAA-GGC-TAG-CCA-GAA-GGA-T-3'
PROBE 1530: 5'-CGA-GCA-AAG-GCC-TGC-TTT-GAA-CAC-TCT-AAT-TTT-TT-3'
PROBE 1537: 5'-TTC-AAC-TAC-GAG-CTT-TTT-AAC-TGC-AAC-AAC-TTT-3'

Two additional oligonucleotides useful with the foregoing include:
PROBE/PRIMER 936: 5'-CCGAATTCGT-CGACAACCTGGTTGATCCTGCCAGT-3'
PROBE/PRIMER 935: 5'-CCCGGGATC-CAAGCTTGATCCTTCTGCAGGTTCACC-TAC-3'

Probe/Primer 936 is designed to hybridize to the 18S rDNA gene strand complimentary to Candida yeast 18S rRNA. Oligonucleotides 935 and 936 are designed for use in assays employing amplification, by the polymerase chain reaction method, of almost the entire 18S rRNA gene (rDNA) of Candida yeasts and its relatives. Additional discussion regarding these probes may be had by reference to commonly assigned copending U.S. Ser. No. 420,577, of Weisburg et al. (Docket No. GT2-5.0, entitled "Nucleic Acid Probes and Methods for Detecting Fungi") and to Example 4, below.

Probe Behavior During Hybridization

The specificity of the preferred probes, when utilized pursuant to the procedures of Example 1, may be characterized by the following:

SPECIES SPECIFIC PROBES

PROBE 1349: 100% inclusive and specific for *Candida albicans*
PROBE 1350: 100% inclusive and specific for *Torulopsis glabrata*
PROBE 1353: 100% inclusive for *Candida kefyr*. Slight cross reactivity with some tested *Torulopsis glabrata* isolates
PROBE 1351: 100% inclusive and specific for *Candida krusei*
PROBE 1355: 100% inclusive and specific for *Candida lusitaniae* (A very weak hybridizer)
PROBE 1421: 100% inclusive and specific for *Candida guilliermondii*
PROBE 1453: 100% inclusive and specific for *Yarrowia lipolytica*

GROUP SPECIFIC PROBES

PROBE 1346: 100% inclusive for the group comprised of *Candida albicans*, *C. tropicalis*, and *C. viswanathii*. Light cross-reactivity with one *C. lusitaniae*.
PROBE 1354: 100% inclusive for *Candida albicans*, *C. tropicalis*, *C. viswanathii*, and *C.parapsilosis*
PROBE 1358: 100% inclusive for *Candida albicans*, *C. tropicalis*, *C. viswanathii*, and *C. parapsilosis*
PROBE 1529: 100% inclusive for *Candida albicans*, *C. tropicalis*, *C. viswanathii*, and *C. parapsilosis*
PROBE 1536: 100% inclusive for *Candida albicans*, *C.tropicalis*, *C. viswanathii*, and *C.parapsilosis*
PROBE 1534: 100% inclusive for *Candida tropicalis*, *C.viswanathii*, and *C. parapsilosis*
PROBE 1535: 100% inclusive for *Candida tropicalis*, *C. viswanathii*, and *C. parapsilosis*

PAN-GENERIC PROBES

PROBE 1530: Hybridizes to most fungi
PROBE 1537: Hybridizes to most fungi

EXAMPLE 1

Dot-Blot Analysis of Probe Hybridization Behavior

Dot-blot analysis, in accordance with well known procedures, involves immobilizing a nucleic acid or a population of nucleic acids on a filter such as nitrocellulose, nylon, or other derivatized membranes which can readily be obtained commercially, specifically for this purpose. Either DNA or RNA can be easily immobilized on such a filter and subsequently can be probed or or tested for hybridization under any of a variety of conditions (i.e., stringencies) with nucleotide sequences or probes of interest. Under stringent conditions, probes whose nucleotide sequences have greater complementarity to the target will exhibit a higher level of hybridization than probes containing less complementarity.

Probes of the present invention were tested in a dot-blot format. One hundred nanograms of target RNA, purified by phenol extraction and centrifugation through cesium triflouroacetate gradients, was denatured and spotted on a nylon membrane. Probes were isotopically labelled with the addition of a 32-Phosphorous moiety to the 5' end of the oligonucleotide. Hybridization of probes occurred, at a temperature of 60° C. in the presence of 1.08M sodium chloride, 60 mM sodium phosphate, and 6 mM ethylenediamine tetraacetic acid, pH 7.4. Unhybridized probe was removed by washing at a salt concentration one-third of the hybridization condition. The filters were exposed to X-ray film and the intensity of hybridization signals was evaluated after three hours of exposure. Table 1 summarizes the behavior of the probes and documents the specificity summarized above.

EXAMPLE 2

Dual Probe Hybridization

In actual practice, many applications of these probes would employ a pair of probes being used simultaneously in a "sandwich" hybridization scheme of "capture" probe and "detector" probe as shown in FIG. 2. The capture probe[12] ideally would be a bifunctional polynucleotide manufactured by adding a homopolymeric 3' tail to a probe with high target specificity. The tail would, in turn, hybridize to the complementary homopolymer[11] on a solid surface[10], such as a glass bead or a filter disc. Hybridization of the capture probe[12] to its target[15] in this case Candida yeast rRNA, would complex the target[15] with the solid support[10]. The detector probe[13] advantageously also with some degree of specificity, would be part of a preferred detection scheme relying on radioactivity, fluorescence, chemiluminescence, color, etc. (detection moiety[14]) which would report the presence of the entire hybridization complex.

For specific detection of the primary infectious agent of Candida infection, *Candida albicans,* a combination of probes 5349 and 1529, for example, could be employed with one derivatized to serve as the detector probe, and the other as a capture probe.

EXAMPLE 3

Clinical Diagnosis of Candida Infection from Human Blood, Sputum, or Cerebrospinal Fluid Sample—Screening for the Major Pathogenic Species

*Candida albicans, Candida tropicalis, Candida parapsilosis,* and *Torulopsis* (Candida) *glabrata* summed together account for greater than 95% of all Candida infection. In this example, Probe 1350 plus Probe 1358 (or alternatively, Probe 1529 or Probe 1536) are used as capture probes, that is they are derivatized with a poly-A tail. Probe 1530 or Probe 1537 is tagged so as to function as a detector oligonucleotide.

The clinical sample is preferably processed so as to yield total nucleic acid content such as by sonication, vortexing with glass beads, detergent lysis using an agent such as SDS or chemical treatment, or alternatively yeast cells are partially purified by, for example, employing the DuPont Isolator System, followed by cell lysis. The sample, containing disrupted yeast cells is incubated in the presence of capture probe, detector probe, and ideally magnetic particle beads which have been derivatized with oligo-Thymidine (see Example 2) in a chaotropic buffer such as guanidinium isothiocyanate.

If target molecules (Candida yeast 18S rRNA, of the four aforementioned species) are present, a Bead+Capture Probe+Target+Detector Probe hybridization complex is formed. The exterior presence of a magnet near the bottom of the reaction tube will cause the magnetic particle-hybridization complex to adhere to the interior side of the tube thereby advantageously enabling removal of the unreacted components such as sample matrix, unbound probe, etc. Repeated rehydration and denaturation of the bead-probe-target complex is advantageously performed to enable significant background reduction (as more fully described in Collins U.S. Ser No. 922,155, EPA 87309308.2). In this example, final detection could entail spotting the beads on membrane and assaying by autoradiography.

EXAMPLE 4

Clinical Diagnosis of Candida Infection from Human Sample Employing Polymerase Chain Reaction Amplification of Fungal rDNA Sample processing is designed so as to yield DNA. Probe/Primer 936 and Probe/Primer 935 are employed in conjunction with the clinical sample in a polymerase chain reaction. Resultant material can then be assayed in a "sandwich" hybridization (Example 2) with any of the probes described herein. The polymerase chain reaction can, itself, be made highly specific by employing Probe/Primer 936 in conjunction with, for example, Probe 1346. Detection could subsequently be accomplished using Probe 1349 for capture and Probe 1529 for detection.

EXAMPLE 5

In situ Hybridization as a Cytological Stain

The probes of the present invention can also be advantageously employed as a cytological staining reagent. For example, a sputum sample is applied to a microscope slide. After appropriate fixation and lysis, hybridization with the probes of the present invention is carried out in situ. In this manner, *Candida albicans* could be visualized in a specimen by fluorescently labelling Probe 1349 and examining the slide under a fluorescent microscope.

EXAMPLE 6

Confirmation of *Candida Fungemia* Following Culture

Following a standard cultivation step utilizing the Bactec, Roche Septi-Chek, or DuPont Isolator, colony or liquid culture is tested for, for example, *Torulopsis glabrata,* employing Probes 1350 and 1530 in the procedures described in Example 2. Of great advantage is that pure culture is not necessary.

It will be readily appreciated by those skilled in the art that various modifications to the procedures or probes set forth herein may be made without departing from either the spirit or scope of the present invention. In particular, when modifications of the probes such as by deleting one or two end nucleotides with accompanying adjustments in hybridization conditions are to be deemed equivalent.

TABLE 1

DOTBLOT HYBRIDIZATION DATA

| NAME/STRAIN | | 1346 | 1349 | 1350 | 1353 | 1351 | 1354 | 1355 | 1358 | 1421 | 1453 |
|---|---|---|---|---|---|---|---|---|---|---|---|
| *Alternaria alternata* | 13963 | − | − | − | − | − | − | − | − | − | − |
| *Agaricus brunnescens* | n5829 | − | − | − | − | − | − | − | − | − | − |
| *Aspergillus flavus* | 10124 | − | − | − | − | − | − | − | − | − | − |
| *Aspergillus fumigatus* | 36607 | − | − | − | − | − | − | − | − | − | − |
| *Aspergillus nidulans* | 10074 | − | − | − | − | − | − | − | − | − | − |
| *Aspergillus niger* | 16888 | − | − | − | − | − | − | − | − | − | − |
| *Aspergillus parasiticus* | 15517 | − | − | − | − | − | − | − | − | − | − |
| *Aspergillus terreus* | 46941 | − | − | − | − | − | − | − | − | − | − |
| *Aspergillus versicolor* | 95776 | − | − | − | − | − | − | − | − | − | − |
| *Blastomyces dermatitidis* | 60916 | − | − | − | − | − | − | − | − | − | − |
| *Byssochlamys fulva* | 10099 | − | − | − | − | − | − | − | − | − | − |
| *Candida albicans* | 11006 | + | + | − | − | − | + | − | + | − | − |
| *Candida albicans* | 14053 | + | + | − | − | − | + | − | + | − | − |
| *Candida albicans* | 18804 | + | + | − | − | − | + | − | + | − | − |
| *Candida albicans* | 24433 | + | + | − | − | − | + | − | + | − | − |
| *Candida albicans* | 36232 | + | + | − | − | − | + | − | + | − | − |
| *Candida albicans* | 60193 | + | + | − | − | − | + | − | + | − | − |
| *Candida guilliermondii* | 6260 | − | − | − | − | − | − | − | − | + | − |
| *Candida kefyr* | 4135 | − | − | − | + | − | − | − | − | − | − |
| *Candida kefyr* | 46764 | − | − | − | + | − | − | − | − | − | − |
| *Candida krusei* | 6258 | − | − | − | − | + | − | − | − | − | − |
| *Candida lusitaniae* | 42720 | +− | − | − | − | − | − | +− | − | − | − |
| *Candida parapsilosis* | 22019 | − | − | − | − | − | + | − | + | − | − |
| *Candida rugosa* | 58964 | − | − | − | − | − | − | − | − | − | − |
| *Candida tropicalis* | 750 | + | − | − | − | − | + | − | + | − | − |
| *Candida tropicalis* | 13803 | + | − | − | − | − | + | − | + | − | − |
| *Candida tropicalis* | 42678 | + | − | − | − | − | + | − | + | − | − |
| *Candida utilis* | 9226 | − | − | − | − | − | − | − | − | − | − |
| *Candida viswanathii* | 22981 | + | − | − | − | − | + | − | + | − | − |
| *Chrysosporium keratinophilum* | 14803 | − | − | − | − | − | − | − | − | − | − |
| *Cladosporium castellani* | 24788 | − | − | − | − | − | − | − | − | − | − |
| *Cryptococcus neoformans* | 14116 | − | − | − | − | − | − | − | − | − | − |
| *Cryptococcus neoformans* | 32045 | − | − | − | − | − | − | − | − | − | − |
| *Cyathus stercoreus* | n6473 | − | − | − | − | − | − | − | − | − | − |
| *Entomophthora virulenta* | 14207 | − | − | − | − | − | − | − | − | − | − |
| *Epidermophyton floccosum* | 52066 | − | − | − | − | − | − | − | − | − | − |
| *Filobasidiella neoformans* | 6352 | − | − | − | − | − | − | − | − | − | − |
| *Fusarium oxysporum* | 16322 | − | − | − | − | − | − | − | − | − | − |
| *Hansenula polymorpha* | 34438 | − | − | − | − | − | − | − | − | − | − |
| *Histoplasma capsulatum* | 12700 | − | − | − | − | − | − | − | − | − | − |
| *Geotrichum candidum* | 34614 | − | − | − | − | − | − | − | − | − | − |
| *Lipomyces starkeyi* | n11557 | − | − | − | − | − | − | − | − | − | − |
| *Metschnikowia bicuspidata* | 22297 | − | − | − | − | − | − | − | − | − | − |
| *Microsporum racemosum* | 38556 | − | − | − | − | − | − | − | − | − | − |
| *Morchella crassipes* | 18408 | − | − | − | − | − | − | − | − | − | − |
| *Mucor rouxii* | 24905 | − | − | − | − | − | − | − | − | − | − |
| *Neurospora crassa* | 14692 | − | − | − | − | − | − | − | − | − | − |
| *Neurospora sitophila* | 36935 | − | − | − | − | − | − | − | − | − | − |
| *Paracoccidioides brasiliensis* | 48093 | − | − | − | − | − | − | − | − | − | − |
| *Penicillium chrysogenum* | 10106 | − | − | − | − | − | − | − | − | − | − |
| *Penicillium digitatum* | 48113 | − | − | − | − | − | − | − | − | − | − |
| *Penicillium notatum* | 9179 | − | − | − | − | − | − | − | − | − | − |
| *Phycomyces blakesleeanus* | n1464 | − | − | − | − | − | − | − | − | − | − |
| *Pityrosporum ovale* | 14521 | − | − | − | − | − | − | − | − | − | − |
| *Pseudallescheria boydii* | 28169 | − | − | − | − | − | − | − | − | − | − |
| *Rhizopus oligosporus* | 22959 | − | − | − | − | − | − | − | − | − | − |
| *Rhodosporidium toruloides* | 10788 | − | − | − | − | − | − | − | − | − | − |
| *Rhodotorula rubra* | 9449 | − | − | − | − | − | − | − | − | − | − |
| *Saccharomyces cerevisiae* | 18824 | − | − | − | − | − | − | − | − | − | − |
| *Saccharomycodes ludwigii* | n12792 | − | − | − | − | − | − | − | − | − | − |
| *Schizosaccharomyces octosporus* | 4206 | − | − | − | − | − | − | − | − | − | − |
| *Sporothrix schenkii* | 14284 | − | − | − | − | − | − | − | − | − | − |
| *Taphrina deformans* | nT857 | − | − | − | − | − | − | − | − | − | − |
| *Torulopsis glabrata* | 2001 | − | − | + | − | − | − | − | − | − | − |
| *Tremella mesenterica* | 42219 | − | − | − | − | − | − | − | − | − | − |
| *Trichophyton mentagrophytes* | 28185 | − | − | − | − | − | − | − | − | − | − |
| *Trichophyton rubrum* | 28188 | − | − | − | − | − | − | − | − | − | − |
| *Trichosporon beigelii* | 28592 | − | − | − | − | − | − | − | − | − | − |
| *Trichosporon capitatum* | 10663 | − | − | − | − | − | − | − | − | − | − |
| *Ustilago maydis* | j1402 | − | − | − | − | − | − | − | − | − | − |
| *Verticillium dahliae* | 16535 | − | − | − | − | − | − | − | − | − | − |
| *Yarrowia lipolytica* | 18942 | − | − | − | − | − | − | − | − | − | − |

TOTAL = 72
EXCLUSIVITY

| | | 1346 | 1349 | 1350 | 1353 | 1351 | 1354 | 1355 | 1358 | 1421 | 1453 |
|---|---|---|---|---|---|---|---|---|---|---|---|
| HUMAN/CaSKi | | − | − | − | − | − | − | − | − | − | − |
| *Staphylococcus aureus* | GT2047 | − | − | − | − | − | − | − | − | − | − |
| *Escherichia coli* | 12036 | − | − | − | − | − | − | − | − | − | − |
| *Candida albicans* (n = 47) | | | | | | | | | | | |

TABLE 1-continued

DOTBLOT HYBRIDIZATION DATA

| NAME/STRAIN | PROBE | | | | | | | | | |
|---|---|---|---|---|---|---|---|---|---|---|
| | 1346 | 1349 | 1350 | 1353 | 1351 | 1354 | 1355 | 1358 | 1421 | 1453 |
| 151-87 | + | + | − | − | − | + | − | + | − | − |
| 184-87 | + | + | − | − | − | + | − | + | − | − |
| 192-87 | + | + | − | − | − | + | − | + | − | − |
| 738-88 | + | + | − | − | − | + | − | + | − | − |
| 784-88 | + | + | − | − | − | + | − | + | − | − |
| 819-88 | + | + | − | − | − | + | − | + | − | − |
| 854-88 | + | + | − | − | − | + | − | + | − | − |
| 864-88 | + | + | − | − | − | + | − | + | − | − |
| 875-88 | + | + | − | − | − | + | − | + | − | − |
| 876-88 | + | + | − | − | − | + | − | + | − | − |
| 889-88 | + | + | − | − | − | + | − | + | − | − |
| 892-88 | + | + | − | − | − | + | − | + | − | − |
| 896-88 | + | + | − | − | − | + | − | + | − | − |
| 901-88 | + | + | − | − | − | + | − | + | − | − |
| 903-88 | + | + | − | − | − | + | − | + | − | − |
| 904-88 | + | + | − | − | − | + | − | + | − | − |
| 917-88 | + | + | − | − | − | + | − | + | − | − |
| 921-88 | + | + | − | − | − | + | − | + | − | − |
| 925-88 | + | + | − | − | − | + | − | + | − | − |
| 926-88 | + | + | − | − | − | + | − | + | − | − |
| 939-88 | + | + | − | − | − | + | − | + | − | − |
| 943-88 | + | + | − | − | − | + | − | + | − | − |
| 946-88 | + | + | − | − | − | + | − | + | − | − |
| 966-88 | + | + | − | − | − | + | − | + | − | − |
| 993-68 | + | + | − | − | − | + | − | + | − | − |
| 161-87 | + | + | − | − | − | + | − | + | − | − |
| 162-87 | + | + | − | − | − | + | − | + | − | − |
| 190-87 | + | + | − | − | − | + | − | + | − | − |
| 203-87 | + | + | − | − | − | + | − | + | − | − |
| 207-87 | + | + | − | − | − | + | − | + | − | − |
| 223-87 | + | + | − | − | − | + | − | + | − | − |
| 227-87 | + | + | − | − | − | + | − | + | − | − |
| 258-87 | + | + | − | − | − | + | − | + | − | − |
| 262-87 | + | + | − | − | − | + | − | + | − | − |
| 266-87 | + | + | − | − | − | + | − | + | − | − |
| 291-87 | + | + | − | − | − | + | − | + | − | − |
| 296-87 | + | + | − | − | − | + | − | + | − | − |
| 307-87 | + | + | − | − | − | + | − | + | − | − |
| 308-87 | + | + | − | − | − | + | − | + | − | − |
| 326-87 | + | + | − | − | − | + | − | + | − | − |
| 342-87 | + | + | − | − | − | + | − | + | − | − |
| 662-87 | + | + | − | − | − | + | − | + | − | − |
| 996-87 | + | + | − | − | − | + | − | + | − | − |
| 984-88 | + | + | − | − | − | + | − | + | − | − |
| 1008-88 | + | + | − | − | − | + | − | + | − | − |
| 1018-88 | + | + | − | − | − | + | − | + | − | − |
| *Candida guilliermondii* (n = 4) | | | | | | | | | | |
| 1055-86 | − | − | − | − | − | − | − | + | − | − |
| 350-87 | − | − | − | − | − | − | − | + | − | − |
| 715-88 | − | − | − | − | − | − | − | + | − | − |
| 974-88 | − | − | − | − | − | − | − | + | − | − |
| *Candida krusei* (n = 4) | | | | | | | | | | |
| 46-87 | − | − | − | − | + | − | − | − | − | − |
| 528-87 | − | − | − | − | + | − | − | − | − | − |
| 842-88 | − | − | − | − | + | − | − | − | − | − |
| 939-88 | − | − | − | − | + | − | − | − | − | − |
| *Candida* (Yarrowia) *lipolytica* (n = 4) | | | | | | | | | | |
| 0565-84 | − | − | − | − | − | − | − | − | − | − |
| 1034-86 | − | − | − | − | − | − | − | − | − | + |
| 1250-85 | − | − | − | − | − | − | − | − | − | + |
| 453-87 | − | − | − | − | − | − | − | − | − | + |
| *Candida lusitaniae* (n = 4) | | | | | | | | | | |
| 1215-85 | − | − | − | − | − | − | +− | − | − | − |
| 1216-85 | − | − | − | − | − | − | +− | − | − | − |
| 403-87 | − | − | − | − | − | − | +− | − | − | − |
| 964-88 | − | − | − | − | − | − | +− | − | − | − |
| *Candida parapsilosis* (n = 8) | | | | | | | | | | |
| 175-87 | − | − | − | − | − | + | − | + | − | − |
| 176-87 | − | − | − | − | − | + | − | + | − | − |
| 491-87 | − | − | − | − | − | + | − | + | − | − |
| 492-87 | − | − | − | − | − | + | − | + | − | − |
| 746-88 | − | − | − | − | − | + | − | + | − | − |
| 754-88 | − | − | − | − | − | + | − | + | − | − |
| 828-88 | − | − | − | − | − | + | − | + | − | − |
| 951-88 | − | − | − | − | − | + | − | + | − | − |
| *Candida* (kefyr) *pseudotropicalis* (n = 4) | | | | | | | | | | |
| 0914-86 | − | − | − | + | − | − | − | − | − | − |

TABLE 1-continued
DOTBLOT HYBRIDIZATION DATA

| NAME/STRAIN | PROBE | | | | | | | | | |
|---|---|---|---|---|---|---|---|---|---|---|
| | 1346 | 1349 | 1350 | 1353 | 1351 | 1354 | 1355 | 1358 | 1421 | 1453 |
| 1001-88 | − | − | − | − | + | − | − | − | − | − |
| 1028-86 | − | − | − | − | + | − | − | − | − | − |
| 999-88 | − | − | − | − | + | − | − | − | − | − |
| *Candida tropicalis* (n = 11) | | | | | | | | | | |
| 484-87 | + | − | − | − | − | + | − | + | − | − |
| 784-88 | + | − | − | − | − | + | − | + | − | − |
| 802-88 | + | − | − | − | − | + | − | + | − | − |
| 846-88 | + | − | − | − | − | + | − | + | − | − |
| 997-88 | + | − | − | − | − | + | − | + | − | − |
| 999-88 | + | − | − | − | − | + | − | + | − | − |
| 150-87 | + | − | − | − | − | + | − | + | − | − |
| 210-87 | + | − | − | − | − | + | − | + | − | − |
| 224-87 | + | − | − | − | − | + | − | + | − | − |
| 319-87 | + | − | − | − | − | + | − | + | − | − |
| 573-87 | + | − | − | − | − | + | − | + | − | − |
| *Torulopsis glabrata* (n = 13) | | | | | | | | | | |
| 233-87 | − | − | + | − | − | − | − | − | − | − |
| 260-87 | − | − | + | − | − | − | − | − | − | − |
| 275-87 | − | − | + | − | − | − | − | − | − | − |
| 288-87 | − | − | + | +− | − | − | − | − | − | − |
| 334-87 | − | − | + | +− | − | − | − | − | − | − |
| 359-87 | − | − | + | − | − | − | − | − | − | − |
| 373-87 | − | − | + | − | − | − | − | − | − | − |
| 506-87 | − | − | + | +− | − | − | − | − | − | − |
| 562-87 | − | − | + | − | − | − | − | − | − | − |
| 573-87 | − | − | + | − | − | − | − | − | − | − |
| 701-87 | − | − | + | − | − | − | − | − | − | − |
| 901-88 | − | − | + | − | − | − | − | − | − | − |
| 903-88 | − | − | + | − | − | − | − | − | − | − |

TABLE 2
DOTBLOT HYBRIDIZATION DATA

| NAME/STRAIN | | PROBE | | | | | |
|---|---|---|---|---|---|---|---|
| | | 1529 | 1530 | 1537 | 1534 | 1535 | 1536 |
| *Alternaria alternate* | 13963 | − | + | + | − | − | − |
| *Agaricus brunnescens* | n5829 | − | + | + | − | − | − |
| *Aspergillus flavus* | 10124 | − | + | + | − | − | − |
| *Aspergillus fumigatus* | 36607 | − | + | + | − | − | − |
| *Aspergillus nidulans* | 10074 | − | + | + | − | − | − |
| *Aspergillus niger* | 16888 | − | + | + | − | − | − |
| *Aspergillus parasiticus* | 15517 | − | + | + | − | − | − |
| *Aspergillus terreus* | 46941 | − | + | + | − | − | − |
| *Aspergillus versicolor* | 95776 | − | + | + | − | − | − |
| *Blastomyces dermatitidis* | 60916 | − | + | + | − | − | − |
| *Byssochlamys fulva* | 10099 | − | + | + | − | − | − |
| *Candida albicans* | 11006 | + | + | + | − | − | + |
| *Candida albicans* | 14053 | + | + | + | − | − | + |
| *Candida albicans* | 18804 | + | + | + | − | − | + |
| *Candida albicans* | 24433 | + | + | + | − | − | + |
| *Candida albicans* | 36232 | + | + | + | − | − | + |
| *Candida albicans* | 60193 | + | + | + | − | − | + |
| *Candida guilliermondii* | 6260 | − | + | + | − | − | − |
| *Candida kefyr* | 4135 | − | + | + | − | − | − |
| *Candida kefyr* | 46764 | − | + | + | − | − | − |
| *Candida krusei* | 6258 | − | + | + | − | − | − |
| *Candida lusitaniae* | 42720 | − | − | + | − | − | − |
| *Candida parapsilosis* | 22019 | + | + | + | + | + | + |
| *Candida rugosa* | 58964 | − | + | + | − | − | − |
| *Candida tropicalis* | 750 | + | + | + | + | + | + |
| *Candida tropicalis* | 13803 | + | + | + | + | + | + |
| *Candida tropicalis* | 42678 | + | + | + | + | + | + |
| *Candida utilis* | 9226 | − | + | + | − | − | − |
| *Candida viswanathii* | 22981 | + | + | + | + | + | + |
| *Chrysosporium keratinophilum* | 14803 | − | + | + | − | − | − |
| *Cladosporium castellani* | 24788 | − | + | + | − | − | − |
| *Cryptococcus neoformans* | 14116 | − | + | + | − | − | − |
| *Cryptococcus neoformans* | 32045 | − | + | + | − | − | − |
| *Cyathus stercoreus* | n6473 | − | + | + | − | − | − |
| *Entomophthora virulenta* | 14207 | − | − | − | − | − | − |
| *Epidermophyton floccosum* | 52066 | − | + | + | − | − | − |
| *Filobasidiella neoformans* | 6352 | − | + | + | − | − | − |
| *Fusarium oxysporum* | 16322 | − | − | − | − | − | − |
| *Hansenula polymorpha* | 34438 | − | + | + | − | − | − |
| *Histoplasma capsulatum* | 12700 | − | + | + | − | − | − |
| *Geotrichum candidum* | 34614 | − | + | + | − | − | − |

TABLE 2-continued

DOTBLOT HYBRIDIZATION DATA

| NAME/STRAIN | | PROBE | | | | | |
|---|---|---|---|---|---|---|---|
| | | 1529 | 1530 | 1537 | 1534 | 1535 | 1536 |
| *Lipomyces starkeyi* | n11557 | − | + | + | − | − | − |
| *Metschnikowia bicuspidata* | 22297 | − | − | + | − | − | − |
| *Microsporum racemosum* | 38556 | − | + | + | − | − | − |
| *Morchella crassipes* | 18408 | NT | NT | NT | NT | NT | NT |
| *Mucor rouxii* | 24905 | − | − | − | − | − | − |
| *Neurospora crassa* | 14692 | − | − | − | − | − | − |
| *Neurospora sitophila* | 36935 | − | − | − | − | − | − |
| *Paracoccidioides brasiliensis* | 48093 | − | + | + | − | − | − |
| *Penicillium chrysogenum* | 10106 | − | + | + | − | − | − |
| *Penicillium digitatum* | 48113 | − | + | + | − | − | − |
| *Penicillium notatum* | 9179 | − | + | + | − | − | − |
| *Phycomyces blakesleeanus* | n1464 | − | − | − | − | − | − |
| *Pityrosporum ovale* | 14521 | − | + | + | − | − | − |
| *Pseudallescheria boydii* | 28169 | − | − | − | − | − | − |
| *Rhizopus oligosporus* | 22959 | − | + | − | − | − | − |
| *Rhodosporidium toruloides* | 10788 | − | + | − | − | − | − |
| *Rhodotorula rubra* | 9449 | − | + | − | − | − | − |
| *Saccharomyces cerevisiae* | 18824 | − | + | + | − | − | − |
| *Saccharomycodes ludwigii* | n12792 | − | + | + | − | − | − |
| *Schizosaccharomyces octosporus* | 4206 | − | + | + | − | − | − |
| *Sporothrix schenkii* | 14284 | − | + | + | − | − | − |
| *Taphrina deformans* | nT857 | − | + | − | − | − | − |
| *Torulopsis glabrata* | 2001 | − | + | + | − | − | − |
| *Tremella mesenterica* | 42219 | − | + | − | − | − | − |
| *Trichophyton mentagrophytes* | 28185 | − | + | + | − | − | − |
| *Trichophyton rubrum* | 28188 | − | + | + | − | − | − |
| *Trichosporon beigelii* | 28592 | − | + | + | − | − | − |
| *Trichosporon capitatum* | 10663 | − | − | − | − | − | − |
| *Ustilago maydis* | j1402 | − | + | + | − | − | − |
| *Verticillium dahliae* | 16535 | − | − | − | − | − | − |
| *Yarrowia lipolytica* | 18942 | − | − | + | − | − | − |
| TOTAL = 72 | | | | | | | |
| EXCLUSIVITY | | | | | | | |
| HUKAN/CaSKi | | − | + | +− | − | − | − |
| *Staphylococcus aureus* | GT2047 | − | − | − | − | − | − |
| *Escherichia coli* | 12036 | − | − | − | − | − | − |
| Stool RNA | | − | − | − | − | − | − |
| Wheat germ RNA | | − | − | + | − | − | − |
| *Candida albicans* (n = 47) | | | | | | | |
| 151-87 | | + | + | + | − | − | + |
| 184-87 | | + | + | + | − | − | + |
| 192-87 | | + | + | + | − | − | + |
| 738-88 | | + | + | + | − | − | + |
| 784-88 | | + | + | + | − | − | + |
| 819-88 | | + | + | + | − | − | + |
| 854-88 | | + | + | + | − | − | + |
| 864-88 | | + | + | + | − | − | + |
| 875-88 | | + | + | + | − | − | + |
| 876-88 | | + | + | + | − | − | + |
| 889-88 | | + | + | + | − | − | + |
| 892-88 | | + | + | + | − | − | + |
| 896-88 | | + | + | + | − | − | + |
| 901-88 | | + | + | + | − | − | + |
| 903-88 | | + | + | + | − | − | + |
| 904-88 | | + | + | + | − | − | + |
| 917-88 | | + | + | + | − | − | + |
| 921-88 | | + | + | + | − | − | + |
| 925-88 | | + | + | + | − | − | + |
| 926-88 | | + | + | + | − | − | + |
| 939-88 | | + | + | + | − | − | + |
| 943-88 | | + | + | + | − | − | + |
| 946-88 | | + | + | + | − | − | + |
| 966-88 | | + | + | + | − | − | + |
| 993-88 | | + | + | + | − | − | + |
| 162-87 | | + | + | + | − | − | + |
| 190-87 | | + | + | + | − | − | + |
| 203-87 | | + | + | + | − | − | + |
| 207-87 | | + | + | + | − | − | + |
| 223-87 | | + | + | + | − | − | + |
| 227-87 | | + | + | + | − | − | + |
| 258-87 | | + | + | + | − | − | + |
| 262-87 | | + | + | + | − | − | + |
| 266-87 | | + | + | + | − | − | + |
| 291-87 | | + | + | + | − | − | + |
| 296-87 | | + | + | + | − | − | + |
| 307-87 | | + | + | + | − | − | + |
| 308-87 | | + | + | + | − | − | + |
| 326-87 | | + | + | + | − | − | + |

TABLE 2-continued

DOTBLOT HYBRIDIZATION DATA

| NAME/STRAIN | PROBE | | | | | |
|---|---|---|---|---|---|---|
| | 1529 | 1530 | 1537 | 1534 | 1535 | 1536 |
| 342-87 | + | + | + | − | − | + |
| 662-87 | + | + | + | − | − | + |
| 996-87 | + | + | + | − | − | + |
| 984-88 | + | + | + | − | − | + |
| 1008-88 | + | + | + | − | − | + |
| 1018-88 | + | + | + | − | − | + |
| *Candida guilliermondii* (n = 4) | | | | | | |
| 1055-86 | − | + | + | − | − | − |
| 350-87 | − | + | + | − | − | − |
| 715-88 | − | + | + | − | − | − |
| 974-88 | − | + | + | − | − | − |
| *Candida krusei* (n = 4) | | | | | | |
| 46-87 | − | + | + | − | − | − |
| 528-87 | − | + | + | − | − | − |
| 842-88 | − | + | + | − | − | − |
| 939-88 | − | + | + | − | − | − |
| *Candida* (Yarrowia) *lipolytica* (n = 4) | | | | | | |
| 0565-84 | − | − | + | − | − | − |
| 1034-86 | − | +− | + | − | − | − |
| 1250-85 | − | − | + | − | − | − |
| 453-87 | − | − | + | − | − | − |
| *Candida lusitaniae* (n = 4) | | | | | | |
| 1215-85 | − | − | + | − | − | − |
| 1216-85 | − | − | + | − | − | − |
| 403-87 | − | − | + | − | − | − |
| 964-88 | − | − | + | − | − | − |
| *Candida parapsilosis* (n = 8) | | | | | | |
| 175-87 | + | + | + | + | + | + |
| 176-87 | + | + | + | + | + | + |
| 491-87 | + | + | + | + | + | + |
| 492-87 | + | + | + | + | + | + |
| 746-88 | + | + | + | + | + | + |
| 754-88 | + | + | + | + | + | + |
| 828-88 | + | + | + | + | + | + |
| 951-88 | + | + | + | + | + | + |
| *Candida* (kefyr) *pseudotropicalis* (n = 4) | | | | | | |
| 0914-86 | − | + | + | − | − | − |
| 1001-88 | − | + | + | − | − | − |
| 1028-86 | − | + | + | − | − | − |
| 999-88 | − | + | + | − | − | − |
| *Candida tropicalis* (n = 11) | | | | | | |
| 484-87 | + | + | + | + | + | + |
| 784-87 | + | + | + | + | + | + |
| 802-87 | + | + | + | + | + | + |
| 846-88 | + | + | + | + | + | + |
| 997-88 | + | + | + | + | + | + |
| 999-88 | + | + | + | + | + | + |
| 150-87 | + | + | + | + | + | + |
| 210-87 | + | + | + | + | + | + |
| 224-87 | + | + | + | + | + | + |
| 319-87 | + | + | + | + | + | + |
| 573-87 | + | + | + | + | + | + |
| *Torulopsis glabrata* (n = 13) | | | | | | |
| 233-87 | − | + | + | − | − | − |
| 260-87 | − | + | + | − | − | − |
| 275-87 | − | + | + | − | − | − |
| 288-87 | − | + | + | − | − | − |
| 334-87 | − | + | + | − | − | − |
| 359-87 | − | + | + | − | − | − |
| 373-87 | − | + | + | − | − | − |
| 506-87 | − | + | + | − | − | − |
| 562-87 | − | + | + | − | − | − |
| 573-87 | − | + | + | − | − | − |
| 701-87 | − | + | + | − | − | − |
| 901-88 | − | + | + | − | − | − |
| 903-88 | − | + | + | − | − | − |

What is claimed is:

1. An isolated nucleic acid probe which hybridizes to 18S rRNA or rDNA of pathogenic Candida yeasts selected from the group consisting of probes 1346, 1349, 1350, 1351, 1353, 1354, 1355, 1358, 1421, 1453, 1530, 1534, 1535, 1536, 1537, and a nucleotide sequence complementary to any one of said probes.

2. A method for detecting the presence of Candida yeast in a sample comprising:
   a) contacting said sample with at least one nucleic acid probe of claim 1, or a probe consisting of the nucleotide sequence of probe/primer 936;
   b) imposing specific hybridization conditions on the sample and said nucleic acid probe to allow said probe to hybridize specifically to the rRNA or rDNA of Candida yeast, if present in the sample, to form nucleic acid complexes, under conditions which do not allow said probe to form stable hybridized nucleic acid complexes with non-Candida yeast; and c) detecting said nucleic acid complexes as an indication of the presence of Candida yeast in the sample.

3. The method of claim 2, wherein said nucleic acid probe in said contacting step consists of the sequence of probe/primer 936, and said detecting step further comprises contacting the sample with a second nucleic acid probe consisting of a nucleotide sequence selected from the group of probes 1346, 1349, 1350, 1351, 1353, 1354, 1355, 1358, 1421, 1453, 1534, 1535, 1536, probe/primer 935, and a nucleotide sequence complementary to any one of said probes.

4. A nucleic acid probe consisting of the nucleotide sequence of probe 1349, or a nucleotide sequence complementary to probe 1349.

5. A nucleic acid probe consisting of the nucleotide sequence of probe 1350, or a nucleotide sequence complementary to probe 1350.

6. A nucleic acid probe consisting of the nucleotide sequence of any one of probes 1354, 1358, and 1536, or a nucleotide sequence complementary to any one of said probes.

7. A nucleic acid probe consisting of the nucleotide sequence of any one of probes 1534 and 1535, or a nucleotide sequence complementary to any one of said probes.

8. A set of nucleic acid probes comprising at least two probes selected from the group consisting of the probes of claim 1, probe 1529, probe 935, and probe 936.

9. The set of nucleic acid probes of claim 8, wherein said set is selected from the group consisting of
probes 1349 and 1529;
probes 1350 and 1530;
probe 1346, and probe 935 or 936;
probes 1349 and 1529, and probe 935 or 936;
probes 1350 and 1358, and probe 1530 or 1537;
probles 1350 and 1529, and probe 1530 or 1537; and
probes 1350 and 1536, and probe 1530 or 1537.

* * * * *

UNITED STATES PATENT AND TRADEMARK OFFICE
CERTIFICATE OF CORRECTION

PATENT NO. : 5,403,710

DATED : April 4, 1995

INVENTOR(S) : William G. Weisburg et al.

It is certified that error appears in the above-identified patent and that said Letters Patent is hereby corrected as shown below:

Title page, item [56], under "Foreign Patent Documents", delete "0272009 11/1987 European Pat. Off.";

Col. 1, line 35, delete "lusitantae", and insert therefor -- lusitaniae --;

Col. 3, line 38, after "C", delete "." (both occurrences);

Col. 4, line 54, delete "+-" and insert therefor -- +-- --;

Col. 5, line 30, delete "TAA" and insert therefor -- AAA --;

Col. 5, line 34, delete "CtA" and insert therefor -- CAA --;

Col. 5, line 68, delete "complimentary" and insert therefor -- complementary --;

Col. 6, line 64, after "probed", delete "or";

Col. 7, line 10, after "C", delete ".";

Col. 7, line 35, after "target[15]", insert -- , --;

Col. 7, line 36, after "probe[13]", insert -- , --;

Col. 7, line 44, delete "5349" and insert therefor -- 1349 --;

Col. 10, Table 1, under column "1453" for "Yarrowia lipolytica", delete "-" and insert therefor -- + --;

Col. 11 & 12, Table 1, under column "1358" for "1055-86", delete "+" and insert therefor -- - --;

UNITED STATES PATENT AND TRADEMARK OFFICE
CERTIFICATE OF CORRECTION

PATENT NO. : 5,403,710

DATED : April 4, 1995

INVENTOR(S) : William G. Weisburg et al.

It is certified that error appears in the above-identified patent and that said Letters Patent is hereby corrected as shown below:

Col. 11 & 12, Table 1, under column "1358" for "350-87", delete "+" and insert therefor -- - --;

Col. 11 & 12, Table 1, under column "1358" for "715-88", delete "+" and insert therefor -- - --;

Col. 11 & 12, Table 1, under column "1358" for "974-88", delete "+" and insert therefor -- - --;

Col. 11 & 12, Table 1, under column "1421" for "1055-86", delete "-" and insert therefor -- + --;

Col. 11 & 12, Table 1, under column "1421" for "350-87", delete "-" and insert therefor -- + --;

Col. 11 & 12, Table 1, under column "1421" for "715-88", delete "-" and insert therefor -- + --;

Col. 11 & 12, Table 1, under column "1421" for "974-88", delete "-" and insert therefor -- + --; and

UNITED STATES PATENT AND TRADEMARK OFFICE
CERTIFICATE OF CORRECTION

PATENT NO. : 5,403,710
DATED : April 4, 1995
INVENTOR(S) : William G. Weisburg et al.

It is certified that error appears in the above-identified patent and that said Letters Patent is hereby corrected as shown below:

Col. 13, Table 2, after "Alternaria", delete "alternate" and insert therefor -- alternata --.

Signed and Sealed this

Twenty-third Day of December, 1997

Attest:

BRUCE LEHMAN

Attesting Officer

Commissioner of Patents and Trademarks